US00PP27330P3

(12) United States Plant Patent
Williams

(10) Patent No.: US PP27,330 P3
(45) Date of Patent: Nov. 1, 2016

(54) ***TRACHELOSPERMUM ASIATICUM* PLANT NAMED 'FT01'**

(50) Latin Name: *Trachelospermum asiaticum*
Varietal Denomination: FT01

(71) Applicant: Jonathon Williams, Dural (AU)

(72) Inventor: Jonathon Williams, Dural (AU)

( * ) Notice: Subject to any disclaimer, the term of this patent is extended or adjusted under 35 U.S.C. 154(b) by 64 days.

(21) Appl. No.: 14/544,739

(22) Filed: Feb. 10, 2015

(65) Prior Publication Data

US 2016/0234989 P1 Aug. 11, 2016

(30) Foreign Application Priority Data

Feb. 11, 2014 (AU) ..... PBR 2014/027

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Susan McCormick Ewoldt
*Assistant Examiner* — Karen Redden
(74) *Attorney, Agent, or Firm* — Samuel R. McCoy, Jr.

(57) ABSTRACT

'FT01' is a distinctive variety of *Trachelospermum asiaticum* which is characterized by the combination of a dense canopy of foliage, a prostrate growth habit, a low plant height, a high number of flowers and uniformity and stability of these characteristics from generation to generation.

2 Drawing Sheets

Latin name of the genus and species: The Latin name of the genus and species of the novel variety disclosed herein is *Trachelospermum asiaticum.*

Variety denomination: The inventive variety of *Trachelospermum asiaticum* disclosed herein has been given the variety denomination 'FT01'.

BACKGROUND OF THE INVENTION

The present invention relates to a new and distinct perennial variety of *Trachelospermum asiaticum*, which has been given the variety denomination of 'FT01'. Its market class is PLT/226. 'FT01' is intended for use in general landscaping and as a decorative groundcover plant.

Parentage: The *Trachelospermum asiaticum* variety 'FT01' is a partial plant mutation of common, unknown *Trachelospermum asiaticum*. In February of 2010, the inventor discovered a branch mutation occurring on a single stock plant of the species, *Trachelospermum asiaticum*, at his wholesale ornamental plant nursery in Dural, New South Wales, Australia. This mutation exhibited a dense canopy of foliage, a more prostrate growth habit, a lower plant height, and a higher number of flowers when compared to the species. Softwood cuttings were harvested from said branch mutation, repotted and allowed to mature in order to confirm the characteristics initially observed and also to evaluate the stability these characteristics. The cultivar was given the denomination of 'FT01'.

Asexual Reproduction: 'FT01' was first propagated asexually by softwood cuttings in Dural, New South Wales, Australia in February of 2010 and has since been asexually propagated by softwood cuttings through five successive generations. The distinctive characteristics of the inventive 'FT01' variety are stable from generation to generation; clones of the variety produced by asexual reproduction maintain the distinguishing characteristics of the original plant.

SUMMARY OF THE INVENTION

'FT01' is a distinctive variety of *Trachelospermum asiaticum* which is characterized by the combination of a dense canopy of foliage, a prostrate growth habit, a low plant height, and a high number of flowers.

BOTANICAL DESCRIPTION OF THE PLANT

Figure 1:
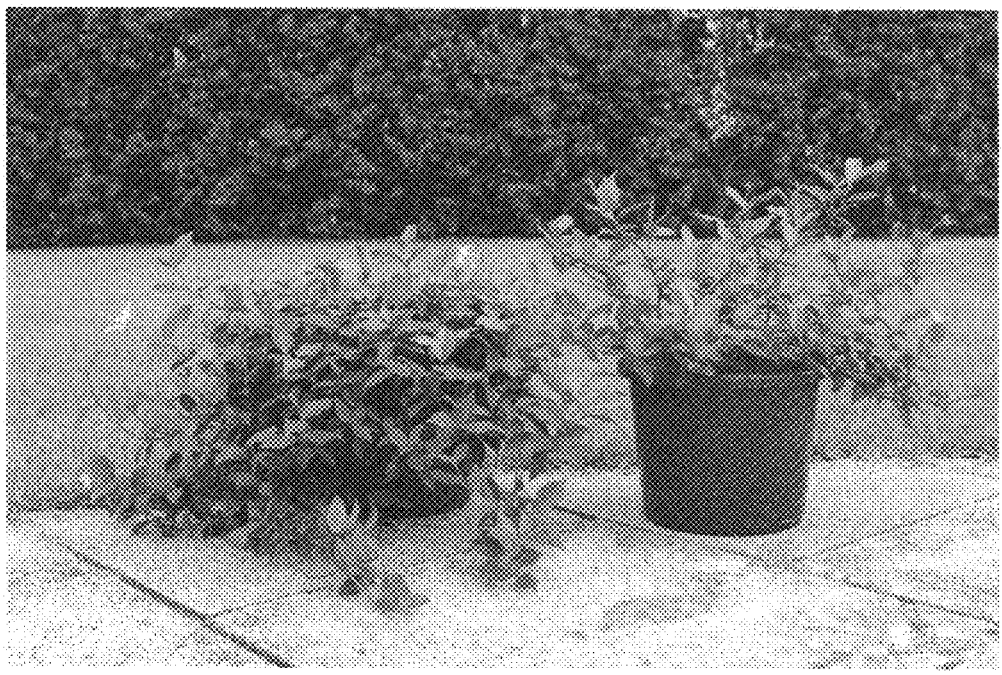
FIG. 1 shows an exemplary specimen of an 18 month old 'FT01' plant in a 400 mm nursery pot, on left, compared to the parent, on right.
Figure 2:
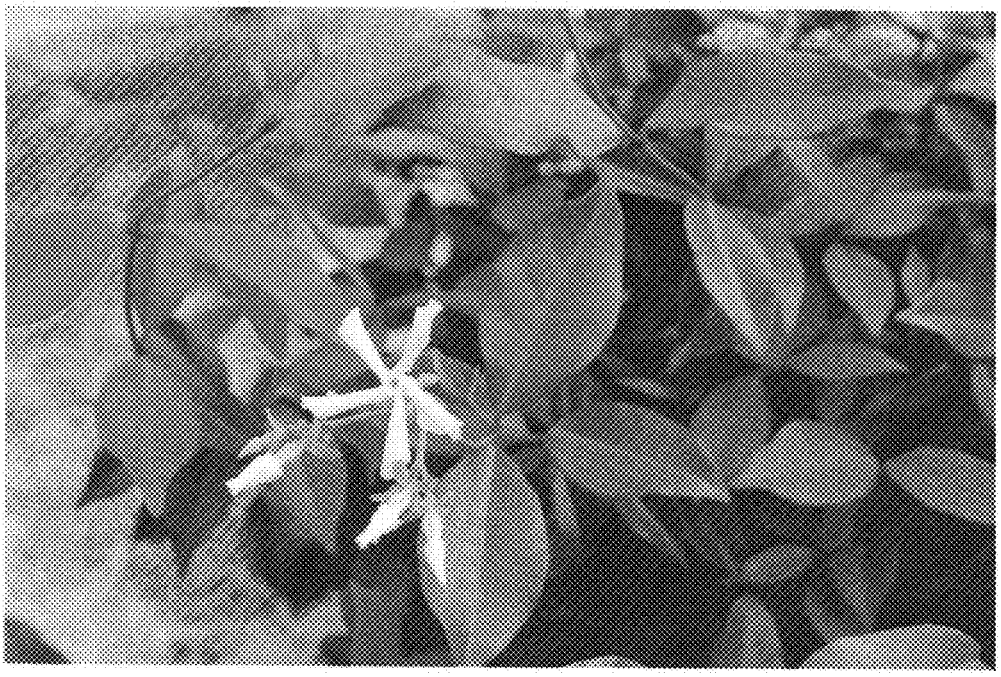
FIG. 2 shows an exemplary inflorescence of an 18 month old 'FT01' plant in a 400 mm nursery pot.

The following is a detailed botanical description of a new and distinct variety of a *Trachelospermum asiaticum* ornamental plant known as 'FT01'. Unless indicated otherwise, the descriptions disclosed herein are based upon observations made from an 18 month old 'FT01' plant, produced in a 400 mm nursery pot in Clarendon, New South Wales, Australia. The observed plant was maintained with granular slow release fertilizer and regularly watered with overhead irrigation. No pest and disease measures were taken.

Those skilled in the art will appreciate that certain characteristics will vary with older or, conversely, younger plants. 'FT01' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on *The Royal Horticultural Society Colour Chart*, The Royal Horticultural Society, London, 2001 edition. Note that generic color descriptions such as 'white' do not exist in the R.H.S. charts and the corresponding R.H.S. colors are quoted.

Technical Description of the Variety.

Plant description:

*Plant habit*.—Perennial sub-shrub or vine; very short height and prostrate, forming a dense mat of foliage. Exhibits a vigorous rate of growth.

*Height*.—15 cm at maturity.

*Width*.—150 cm at maturity.

*Bloom period*.—Late spring and throughout summer.

*Hardiness*.—USDA Zone 8 to 11.

*Propagation*.—Propagation is accomplished using softwood cuttings. Roots well without rooting compound or hormone.

*Time to develop roots*.—Approximately 21 days at 20 degrees Celsius.

*Crop time*.—Approximately eight to ten months are needed to produce a well rooted 15 cm nursery pot, starting from a rooted cutting. Crop time varies with location and production practices.

*Pest and disease susceptibility or resistance*.—No disease or pest problems have been observed.

*Cultural tolerances*.—Adapt to a wide range of soil types except for the most saturated of soil conditions. Prefers partial shade but adapt to both full sun and heavy shade when properly maintained. 'FT01' has good drought and salt tolerance, once established.

Roots: Fibrous root system.

Stem:

*General habit*.—Multiple lateral stems, basally branched and generally lacking a central stem. Produces a milky exudate when wounded or cut.

*Stem strength*.—Medium rigidity.

*Attitude*.—Stems are generally horizontal.

*Stem cross-section*.—Round.

*Stem color*.—200A at 10 nodes below the active growing point.

*Stem dimensions*.—Length is variable and up to 150 cm with a diameter of 2.6 mm, at 10 nodes below the active growing point.

*Stem surface*.—Rough; young stems are lightly pubescent and mature stems are glabrous.

*Internode length*.—22 mm, at 10 nodes below the active growing point.

Foliage:

*Type*.—Deciduous.

*Shape*.—Elliptical.

*Division*.—Simple.

*Apex*.—Acuminate.

*Base*.—Cuneate.

*Venation*.—Pinnate.

*Vein color* (*adaxial surfaces*).—145A.

*Vein color* (*abaxial surfaces*).—Indistinguishable from surrounding foliage.

*Margins*.—Entire.

*Arrangement*.—Opposite.

*Attachment*.—Petiolate.

*Attachment*.—Leathery.

*Surfaces* (*adaxial & abaxial surfaces*).—Glabrous and glossy.

*Mature leaf dimensions*.—Average length, 55 mm; width is 25 mm.

*Leaf color* (*adaxial surface*).—139A in both juvenile and mature leaves.

*Leaf color* (*abaxial surface*).—145A in both juvenile and mature leaves.

*Petiole*.—Approximately 5 mm in length; width is approximately 1.5 mm; color is 145A.

*Stipules*.—Absent.

Inflorescence:

*General*.—Axillary and terminal cymes with 2 to 5 flowers per cymes.

*Dimensions*.—Approximately 75 mm long (including peduncle) and 40 mm wide.

*Peduncle*.—Peduncle dimensions — Average 50 mm in length and 2 mm in diameter. Peduncle color — 145A. Peduncle strength — Medium.

Bud: Shape is oblanceolate; approximately 12 mm in length and 4 mm in width, color is 155C with base 145D.

Flower:

*General*.—Pedicellate, simple and persistent with each flower lasting approximately 6 days. Self cleaning. Strong jasmine-like fragrance.

*Flower aspect*.—Outward to slightly pendulous.

*Corolla shape*.—Campanulate with lower third of the corolla fused into a tube and the outer two-thirds comprised of free, equally-spaced petals.

*Corolla width*.—20 mm.

*Corolla depth*.—12 mm.

*Petal appearance*.—Matte, glabrous.

*Petal arrangement*.—Rotate.

*Petal texture*.—Glabrous.

*Number of petals*.—Five in number.

*Petal shape*.—Cuneate; petals are highly revolute near the apex.

*Petal margin*.—Entire to undulate.

*Petal apex*.—Broad obtuse.

*Petal base*.—Fused; truncate.

*Petal dimensions*.—8.5 mm in length and 7 mm wide, at the widest point.

*Petal color when fully opened* (*upper side*).—155C and near 5D at and near the corolla tube opening.

*Petal color when fully opened* (*under side*).—155C.

*Pedicel*.—Color is 145A; dimensions are approximately 15 mm long and 1.5 mm wide; surface is lightly pubescent.

*Calyx*.—Calyx shape — Campanulate; lower half being fused and upper portion comprised of 5 sepal lobes. Calyx dimensions — Approximately 9 mm across and 4 mm deep. Sepals — Sepal appearance — Glossy and smooth. Sepal arrangement — Rotate. Number of sepal lobes — Five. Sepal lobe shape — Lanceolate. Sepal lobe margin — Entire. Sepal lobe apex — Acute. Sepal lobe base — Fused; truncate. Sepal lobe dimensions — Approximately 4.5 mm from point of fusion to the apex and 3 mm at the widest point.

Reproductive organs: Not observed.

Fruit and seed: Not observed.

Comparisons With Parent Plant

Plants of the new cultivar 'FT01' are similar to the parent in many horticultural characteristics including foliage and flower characteristics, general growth habit and environmental tolerances. However, 'FT01' exhibits a very short plant height when not supported, a denser foliage canopy resulting from shorter internodal spacing, and a prostrate growth habit whereas the parent exhibits a tall plant height of approximately 60 cm when not supported, a more open foliage canopy, and an upright growth habit. Furthermore, 'FT01' exhibits a more floriferous bloom habit by comparison with the parent.

Comparisons With Other Commercial *Trachelospermum*

Plants of the new cultivar 'FT01' are comparable to the commercial variety *Trachelospermum asiaticum* 'Minima' (unpatented) in that both are said to have a shorter plant height compared to the species. However, 'FT01' exhibits larger leaves, larger flowers and is also more floriferous when compared to 'Minima'. Furthermore, 'FT01' exhibits a faster rate of growth compared to the growth rate of 'Minima'.

That which is claimed is:

1. A new and distinct variety of *Trachelospermum asiaticum* plant named 'FT01', substantially as described and illustrated herein.

* * * * *